(12) United States Patent
Booth et al.

(10) Patent No.: US 12,343,513 B2
(45) Date of Patent: *Jul. 1, 2025

(54) END-OF-DOSE DETECTION FOR DRUG DELIVERY SYSTEM

(71) Applicant: Becton, Dickinson and Company, Franklin Lakes, NJ (US)

(72) Inventors: David E. Booth, Frederick, MD (US); Michael Vincent Quinn, East Hanover, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 384 days.

This patent is subject to a terminal disclaimer.

(21) Appl. No.: 17/850,428

(22) Filed: Jun. 27, 2022

(65) Prior Publication Data

US 2022/0323682 A1    Oct. 13, 2022

Related U.S. Application Data

(63) Continuation of application No. 16/160,153, filed on Oct. 15, 2018, now Pat. No. 11,439,767.

(Continued)

(51) Int. Cl.
*A61M 5/315*    (2006.01)
*A61M 5/142*    (2006.01)
(Continued)

(52) U.S. Cl.
CPC ...... *A61M 5/3157* (2013.01); *A61M 5/14248* (2013.01); *A61M 5/2033* (2013.01);
(Continued)

(58) Field of Classification Search
CPC .................................................. A61M 5/3157
See application file for complete search history.

(56) References Cited

U.S. PATENT DOCUMENTS 6,186,982 B1    2/2001    Gross et al.
8,021,357 B2    9/2011    Tanaka et al.
(Continued)

FOREIGN PATENT DOCUMENTS

CN    103857427 A    6/2014
CN    104984438 A    10/2015
(Continued)

*Primary Examiner* — Jenna Zhang
(74) *Attorney, Agent, or Firm* — The Webb Law Firm

(57) ABSTRACT

A drug delivery system having an end-of-dose detection arrangement for injecting a medicament. The system including a container configured to receive a medicament, a drive assembly which, upon actuation, is configured to expel the medicament from the container, a needle for injecting the medicament to a patient, a needle actuator assembly comprising a movable portion biased by a biasing member and configured to move the needle between a pre-use position, a use positon for delivery of the medicament to the patient, and a post-use position after delivery of the medicament is completed, and a tube in fluid communication with the container and the needle, the tube comprising an expandable portion having an expanded state and a non-expanded state, wherein the expandable portion is configured to be in the expanded state upon actuation of the drive assembly and a non-expanded state when the needle is in the post-use positon.

17 Claims, 11 Drawing Sheets

Related U.S. Application Data

(60) Provisional application No. 62/572,722, filed on Oct. 16, 2017.

(51) Int. Cl.
    *A61M 5/20*     (2006.01)
    *A61M 5/24*     (2006.01)
    *A61M 5/50*     (2006.01)
    *A61M 5/31*     (2006.01)

(52) U.S. Cl.
    CPC ...... *A61M 5/2459* (2013.01); *A61M 5/31571* (2013.01); *A61M 5/5086* (2013.01); *A61M 2005/14256* (2013.01); *A61M 2005/206* (2013.01); *A61M 2005/3128* (2013.01); *A61M 5/3158* (2013.01)

(56) References Cited

U.S. PATENT DOCUMENTS

| | | | |
|---|---|---|---|
| 9,821,116 B2 | 11/2017 | Vouillamoz et al. | |
| 10,183,121 B2 | 1/2019 | Cowe | |
| 10,391,245 B2 | 8/2019 | Cronenberg et al. | |
| 11,439,767 B2 * | 9/2022 | Booth | A61M 5/14248 |
| 2002/0123740 A1 * | 9/2002 | Flaherty | A61M 5/1452 604/93.01 |
| 2009/0043278 A1 * | 2/2009 | Tanaka | A61M 5/1452 604/138 |
| 2013/0110049 A1 * | 5/2013 | Cronenberg | A61M 5/1454 604/239 |
| 2014/0207104 A1 * | 7/2014 | Vouillamoz | A61M 5/158 604/179 |
| 2015/0080800 A1 | 3/2015 | Cronenberg | |
| 2015/0182691 A1 | 7/2015 | McLoughlin et al. | |
| 2016/0058941 A1 | 3/2016 | Wu et al. | |
| 2017/0028132 A1 | 2/2017 | Cronenberg et al. | |
| 2017/0348486 A1 | 12/2017 | Andersen et al. | |
| 2017/0354781 A1 | 12/2017 | Cronenberg et al. | |

FOREIGN PATENT DOCUMENTS

| | | |
|---|---|---|
| CN | 105451792 A | 3/2016 |
| EP | 1884259 A1 | 2/2008 |
| JP | 2014521443 A | 8/2014 |
| JP | 2017500996 A | 1/2017 |
| WO | 2006024172 A1 | 3/2006 |
| WO | 2006126653 A1 | 11/2006 |
| WO | 2012110575 A1 | 8/2012 |
| WO | 2013155153 A1 | 10/2013 |
| WO | 2014179774 A1 | 11/2014 |
| WO | 2015081337 A1 | 6/2015 |
| WO | 2016107789 A1 | 7/2016 |

\* cited by examiner

END-OF-DOSE DETECTION FOR DRUG DELIVERY SYSTEM

CROSS-REFERENCE TO RELATED APPLICATION

The present application is a continuation of U.S. application Ser. No. 16/160,153, filed Oct. 15, 2018, entitled "End-of-Dose Detection for Drug Delivery System", which claims priority to U.S. Provisional Application Ser. No. 62/572,722, filed Oct. 16, 2017, entitled "End-of-Dose Detection for Drug Delivery System", the entire disclosures of each of which are hereby incorporated by reference.

BACKGROUND OF THE INVENTION

Field of the Invention

The present disclosure relates generally to an injector device and method for delivering a fluid into the body of a patient by injection and, in particular, to an end-of-dose detection arrangement for preventing movement of the needle actuator during delivery of the fluid and for controlling the withdrawal of the needle from the patient at the end of the dose.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

In accordance with one aspect of the invention, a drug delivery system for injecting a medicament includes a container configured to deliver a medicament, a drive assembly which, upon actuation, is configured to expel the medicament from the container, a needle for injecting the medicament to a patient, a needle actuator assembly comprising a movable portion biased by a biasing member and configured to move the needle between a pre-use position, a use positon for delivery of the medicament to the patient, and a post-use position after delivery of the medicament is completed, and a tube in fluid communication with the container and the needle, the tube comprising an expandable portion having an expanded state and a non-expanded state, wherein the expandable portion is configured to be in the expanded state upon actuation of the drive assembly and a non-expanded state when the needle is in the post-use positon.

The expandable portion of the tube is in the non-expanded state when the needle is in the pre-use positon. The movable portion of the needle actuator assembly engages the expandable portion of the tube when the expandable portion of the tube is in the expanded state. The expandable portion of the tube is configured to be placed in the expanded state by a pressure within the container caused by actuation of the drive assembly. The expandable portion of the tube is configured to change from the expanded state to the non-expanded state when the pressure within the container caused by the actuation of the drive assembly is reduced due to a lack of medicament within the container. The engagement between the needle actuator assembly and the tube is released when the tube enters into the non-expanded state, permitting the needle actuator assembly to move and retract the needle.

The drug delivery system can further include a housing enclosing at least a portion of the container, the drive assembly, the needle, the needle actuator assembly, and the tube. When in the use portion, at least a portion of the needle is extended from the housing in the use positon.

According to one design, the tube can be associated with the needle actuator assembly via a slot provided in a top portion of the needle actuator for holding the tube in place.

The use of the end-of-dose arrangement of the present invention allows the stopper or plunger member to bottom out within the container and to still automatically withdraw the needle from the patient after the end of the dose.

In accordance with another embodiment of the present invention, a drug delivery system for injecting a medicament includes a container configured to deliver a medicament, and a drive assembly which, upon actuation, is configured to expel the medicament from the container. The system also includes a needle for injecting the medicament to a patient, a needle actuator assembly comprising a movable portion biased by a biasing member and configured to move the needle between a pre-use position, a use positon for delivery of the medicament to the patient, and a post-use position after delivery of the medicament is completed, and an end-of-dose detection assembly which prevents movement of the needle actuator during delivery of the medicament.

In certain configurations, the end-of-dose detection assembly includes an expandable portion which expands during delivery of the medicament, and which deflates at the end of dose to allow movement of the needle.

In still other configurations, the expandable portion deflates due to a drop in pressure in a fluid path defined between the container and the needle.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DESCRIPTION OF THE INVENTION

Figure 1:
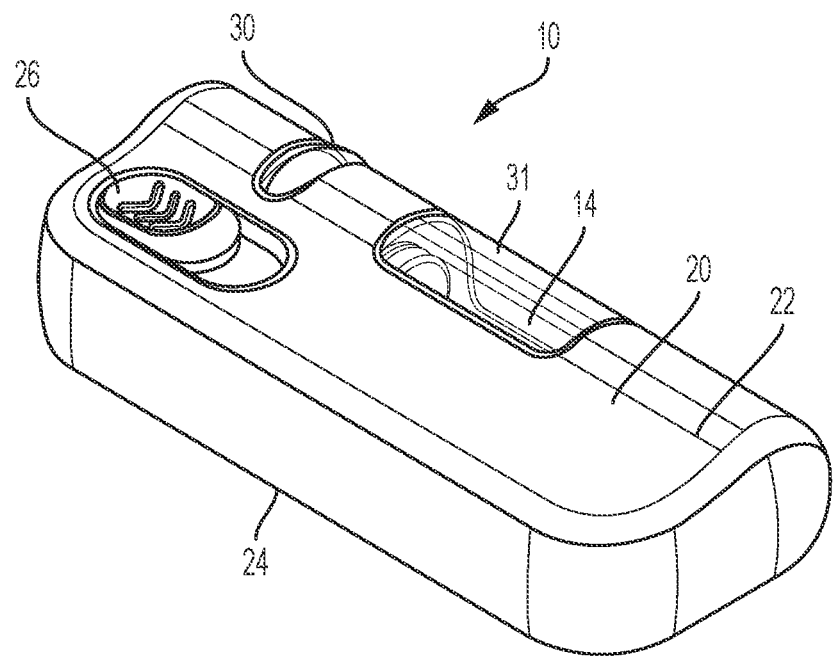
FIG. 1 is a perspective view of a drug delivery system according to one aspect of the present invention.
Figure 2:
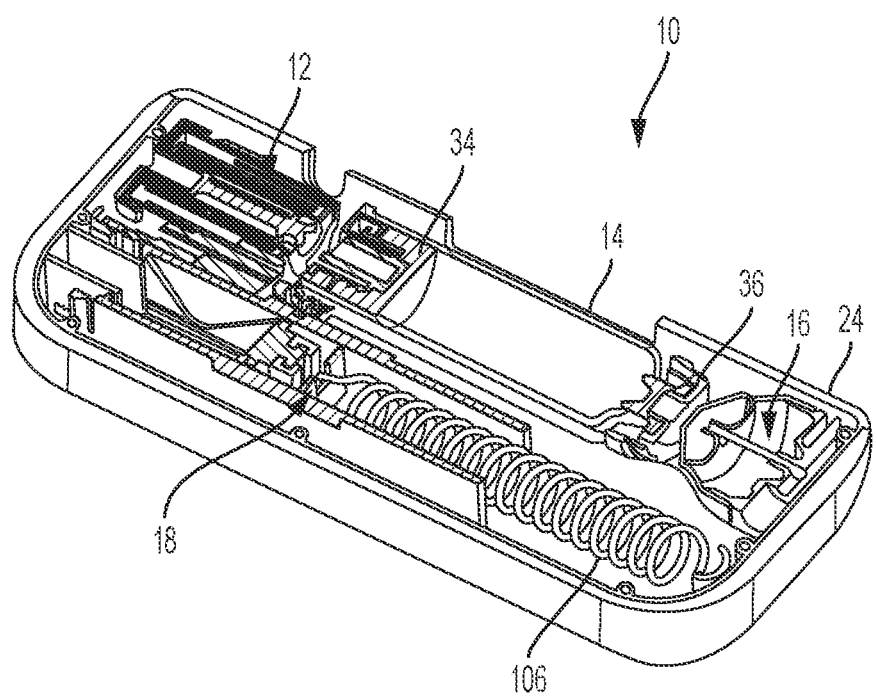
FIG. 2 is a perspective, cross-sectional view of the drug delivery system of FIG. 1 according to one aspect of the present invention.
Figure 3:
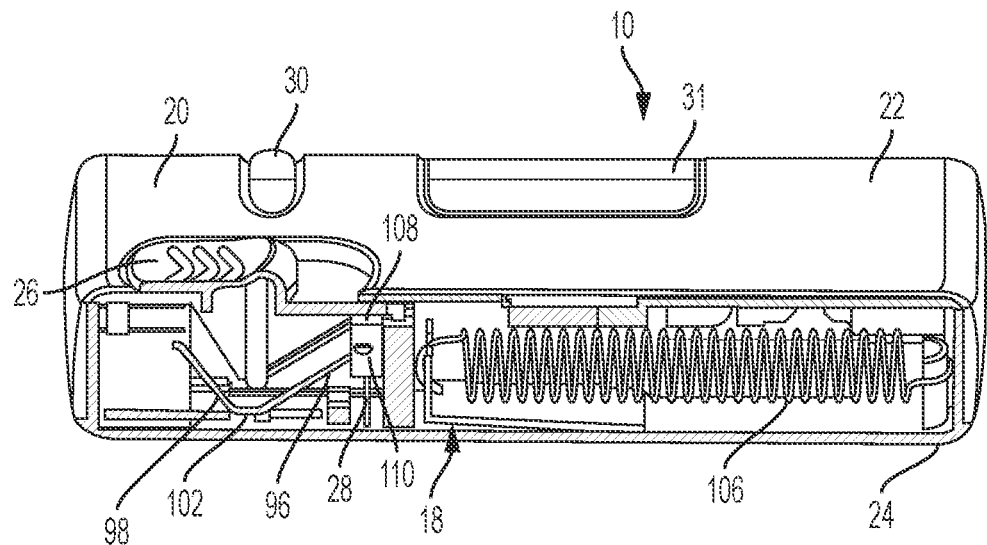
FIG. 3 is a front perspective, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-18, a drug delivery system 10 according to one aspect of the present invention includes a drive assembly 12, a container 14, a valve assembly 16, and a needle actuator assembly 18. The drive assembly 12, the container 14, the valve assembly 16, and the needle actuator assembly 18 are at least partially positioned within a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-18. The specifics of the drive assembly 12, needle actuator assembly 18, and other features of the system 10, are shown and described in U.S. Provisional Application No. 62/347,899, filed Jun. 9, 2016, which is hereby incorporated by reference in its entirety.

Referring again to FIGS. 1-18, the system 10 is configured to operate through the engagement of an actuation button 26 by a user, which results in a needle 28 of the needle actuator assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. WO 2013/155153 and WO 2014/179774, which are hereby incorporated by reference in their entirety. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 4:
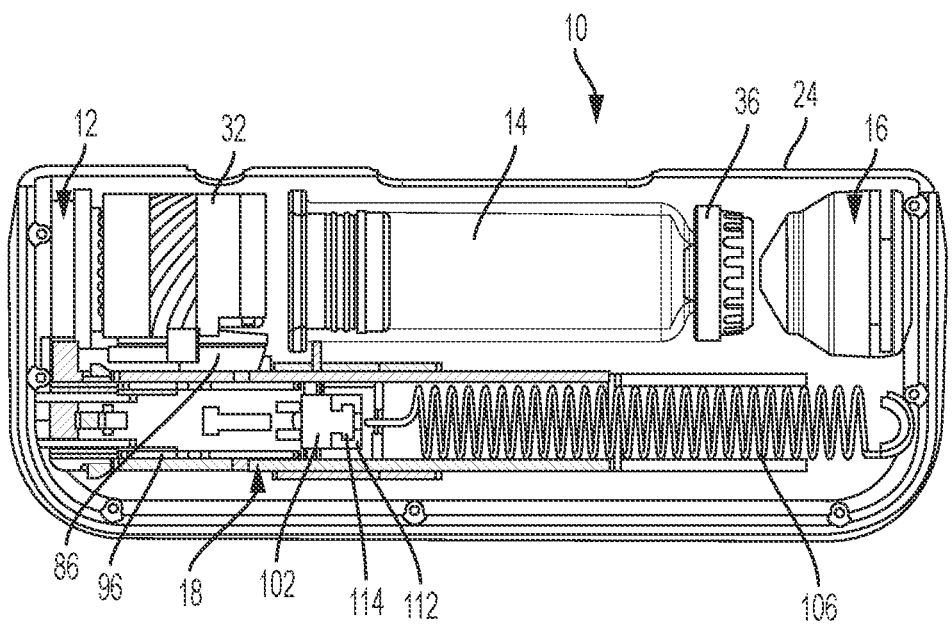
FIG. 4 is a top view of the drug delivery system of FIG. 1 according to one aspect of the present invention, showing a top portion of the housing removed and the drug delivery system in a pre-use position.
Figure 5:
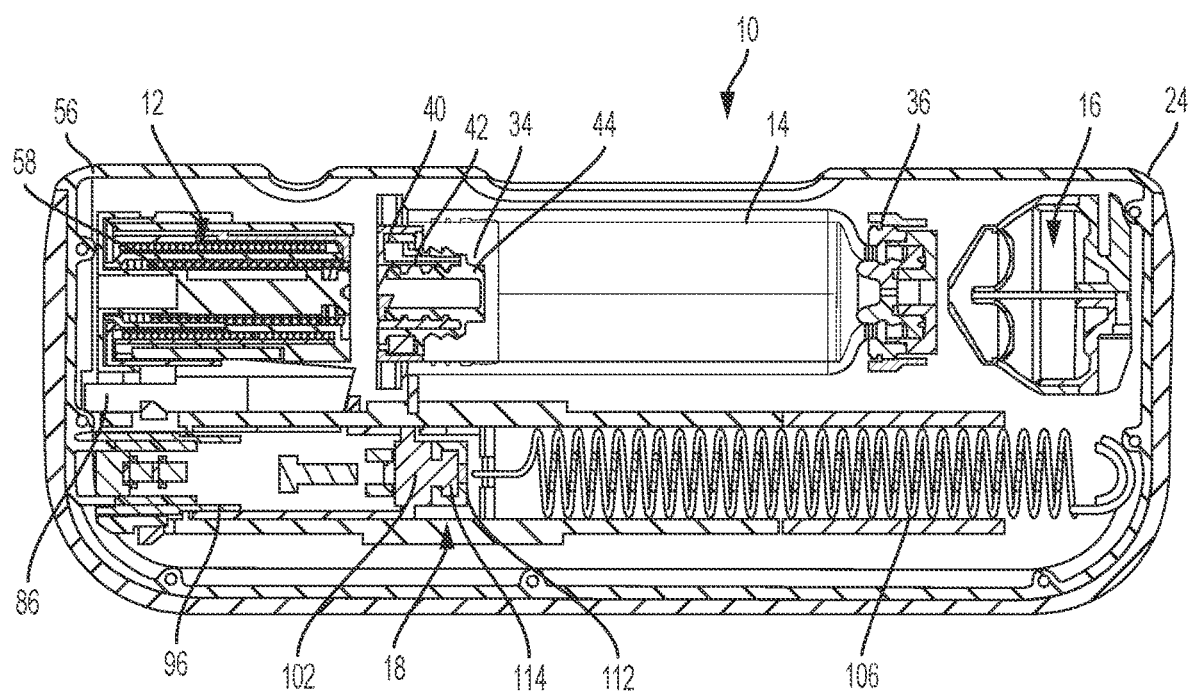
FIG. 5 is a top, cross-sectional view of the drug delivery system of FIG. 1 according to one aspect of the present invention, showing the drug delivery system in a pre-use position.
Figure 6:
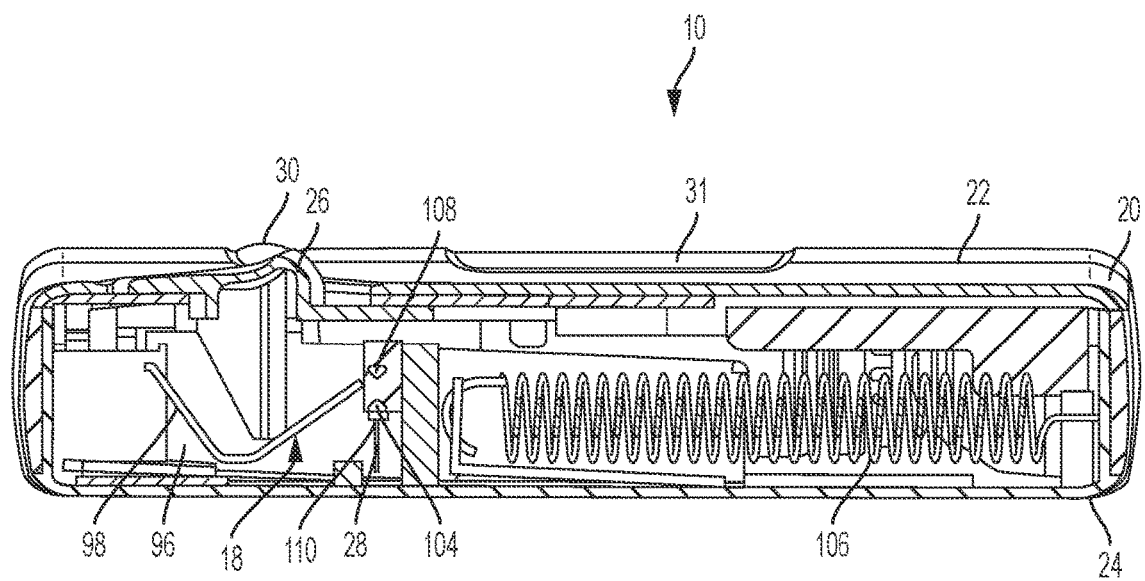
FIG. 6 is a front, cross-sectional view of the drug delivery system of FIG. 1 according to one aspect of the present invention, showing the drug delivery system in a pre-use position.
Figure 7:
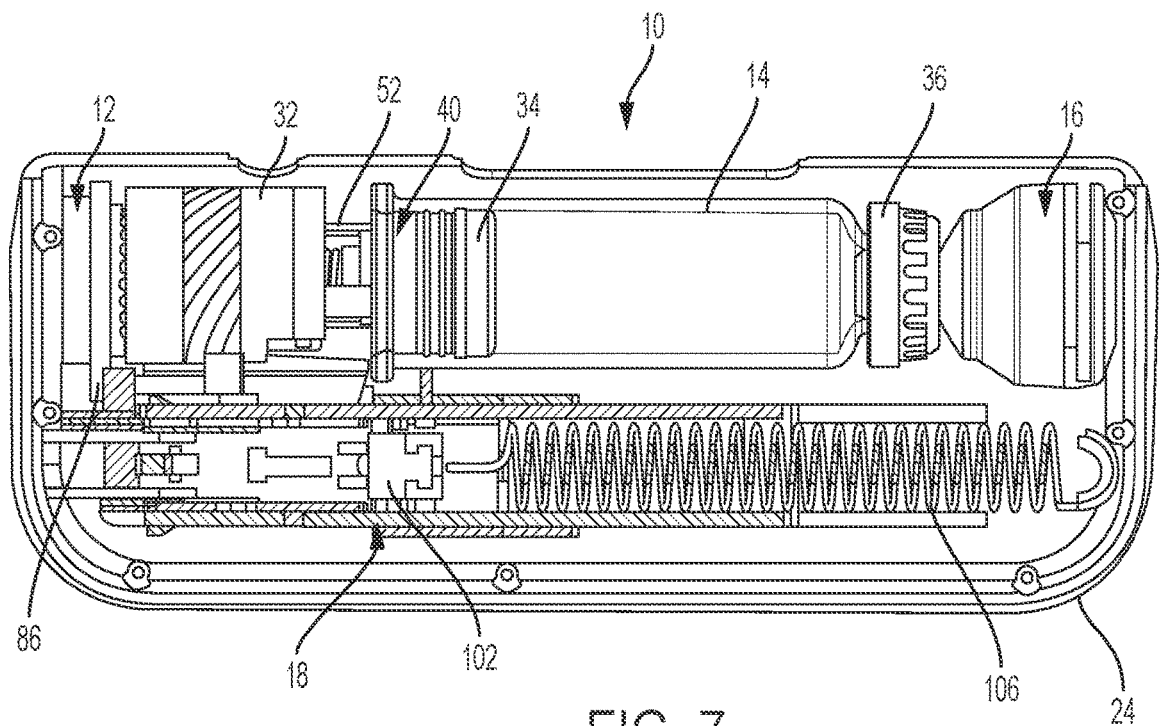
FIG. 7 is a top view of the drug delivery system of FIG. 1 according to one aspect of the present invention, showing a top portion of the housing removed and the drug delivery system in an initial actuation position.
Figure 8:
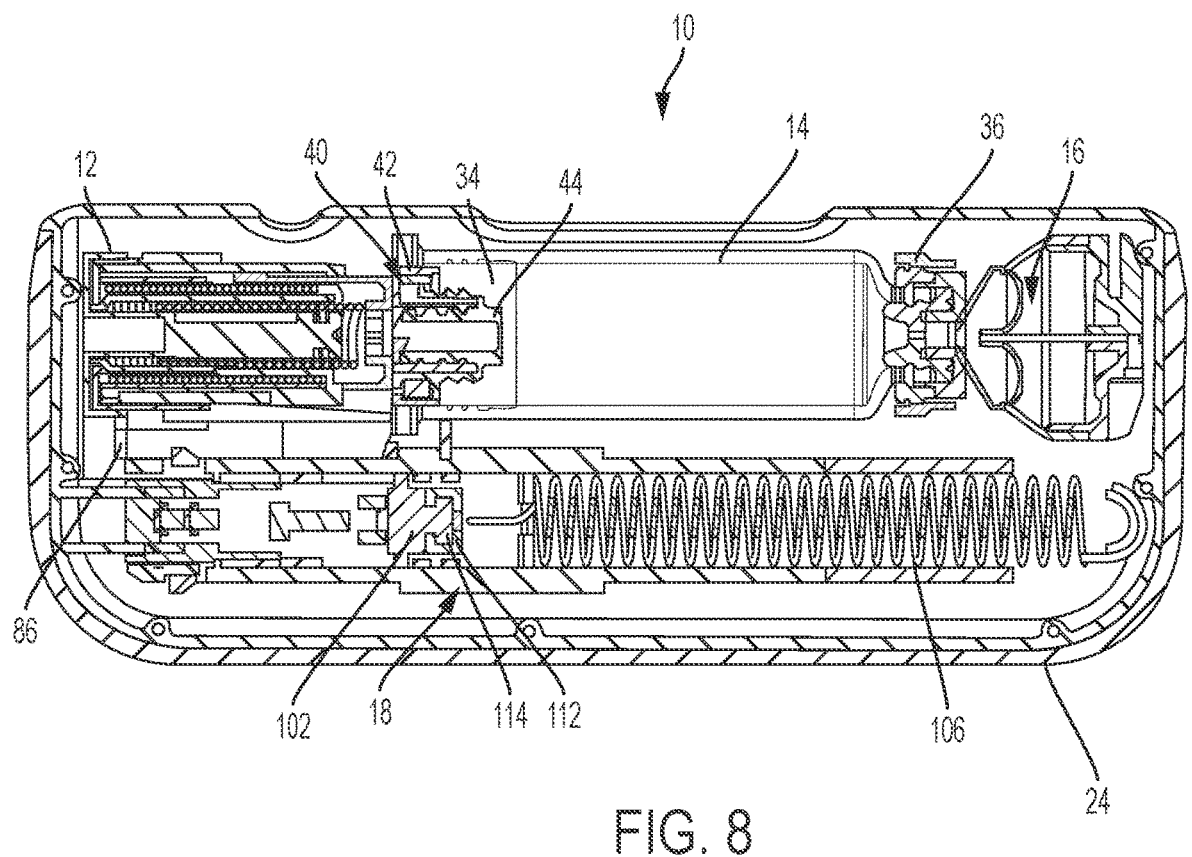
FIG. 8 is a top, cross-sectional view of the drug delivery system of FIG. 1 according to one aspect of the present invention, showing the drug delivery system in an initial actuation position.
Figure 9:
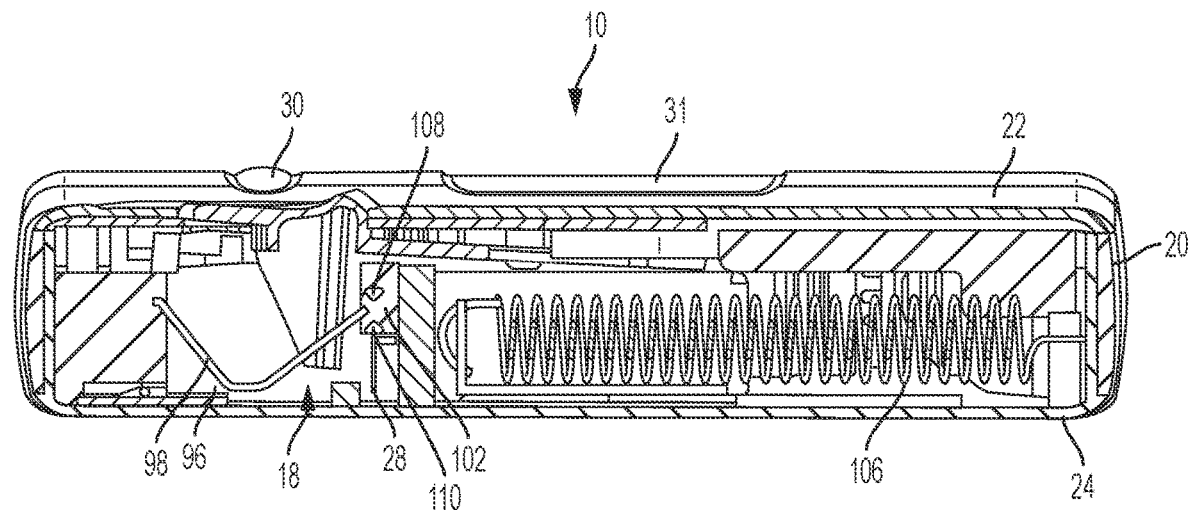
FIG. 9 is a front, cross-sectional view of the drug delivery system of FIG. 1 according to one aspect of the present invention, showing the drug delivery system in an initial actuation position.
Figure 17:
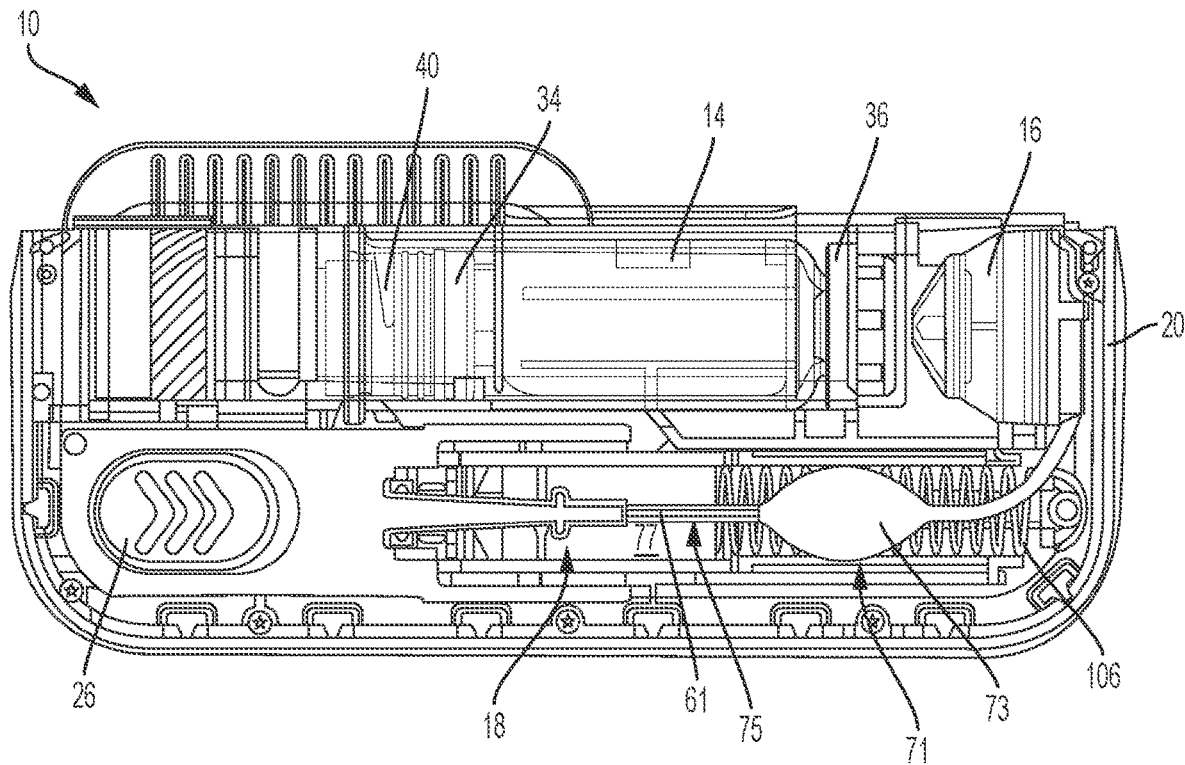
FIG. 17 is a top view of a drug delivery system including an end-of-dose detection arrangement according to one aspect of the present invention, wherein a top portion of the housing is removed and the drug delivery system is in a pre-use position.
Figure 18:
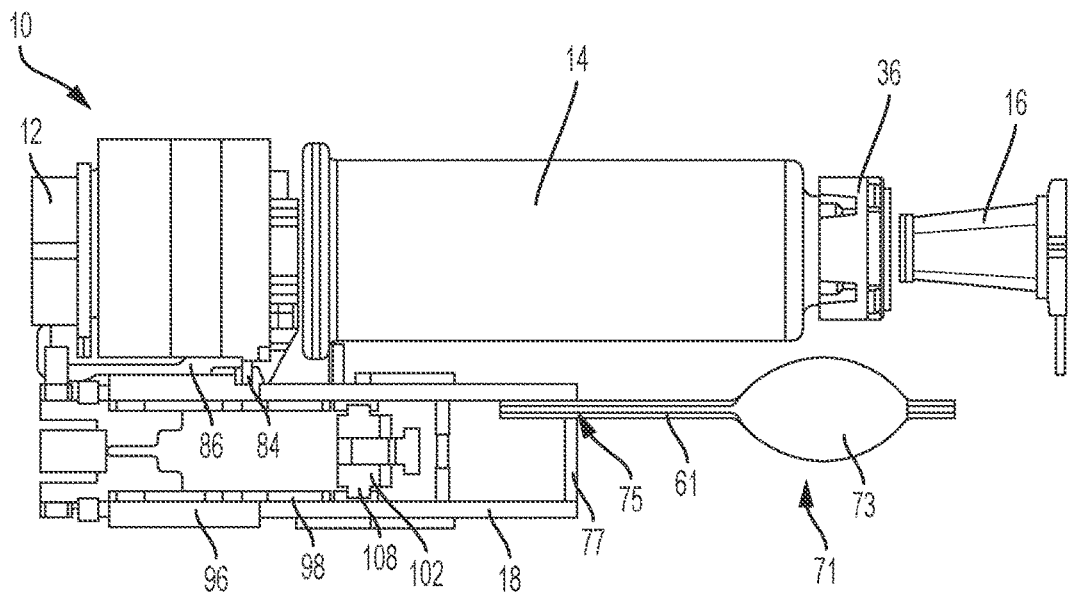
FIG. 18 is a top view of the drug delivery system and end-of-dose detection arrangement of FIG. 17, wherein certain components of the drug delivery system have been removed.

Referring to FIGS. 4-6, during a pre-use position of the system 10, the container 14 is spaced from the drive assembly 12 and the valve assembly 16, and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube 61, as shown in FIGS. 17 and 18. It can be appreciated that other suitable arrangements can be provided to establish fluid communication between the medicament within the container and the needle 28. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
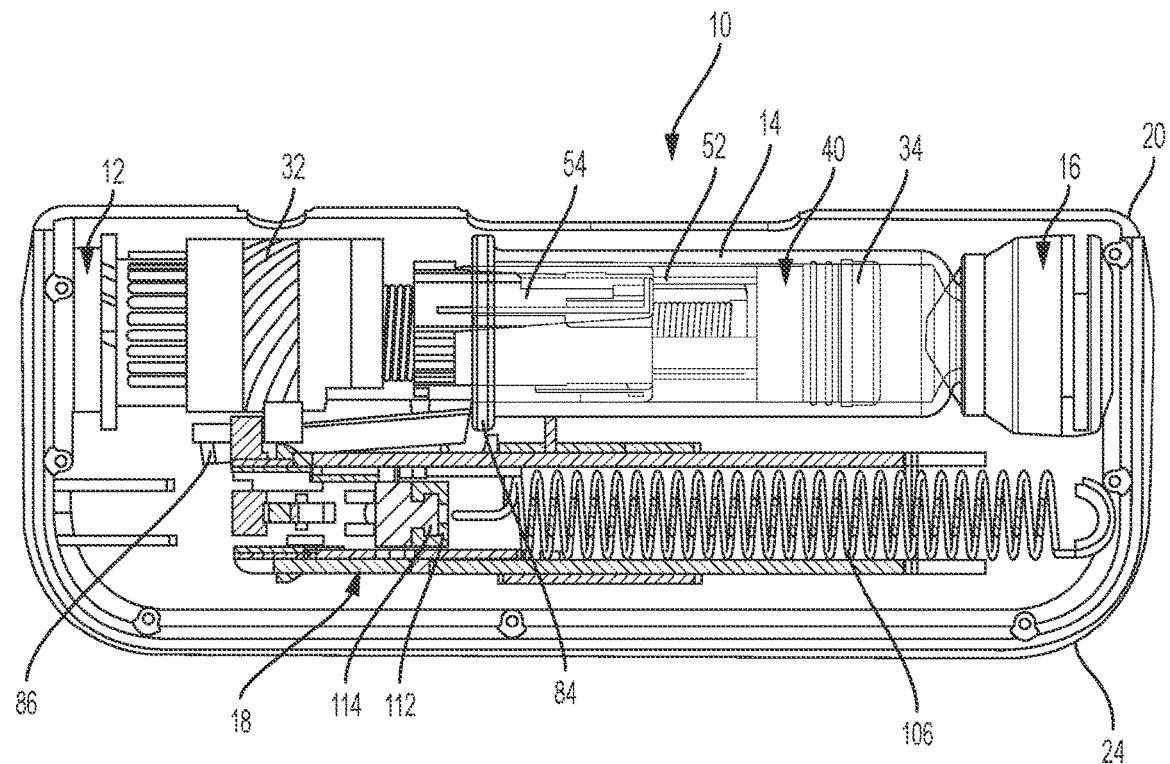
FIG. 10 is a top view of the drug delivery system of FIG. 1 according to one aspect of the present invention, showing a top portion of the housing removed and the drug delivery system in a use position.
Figure 11:
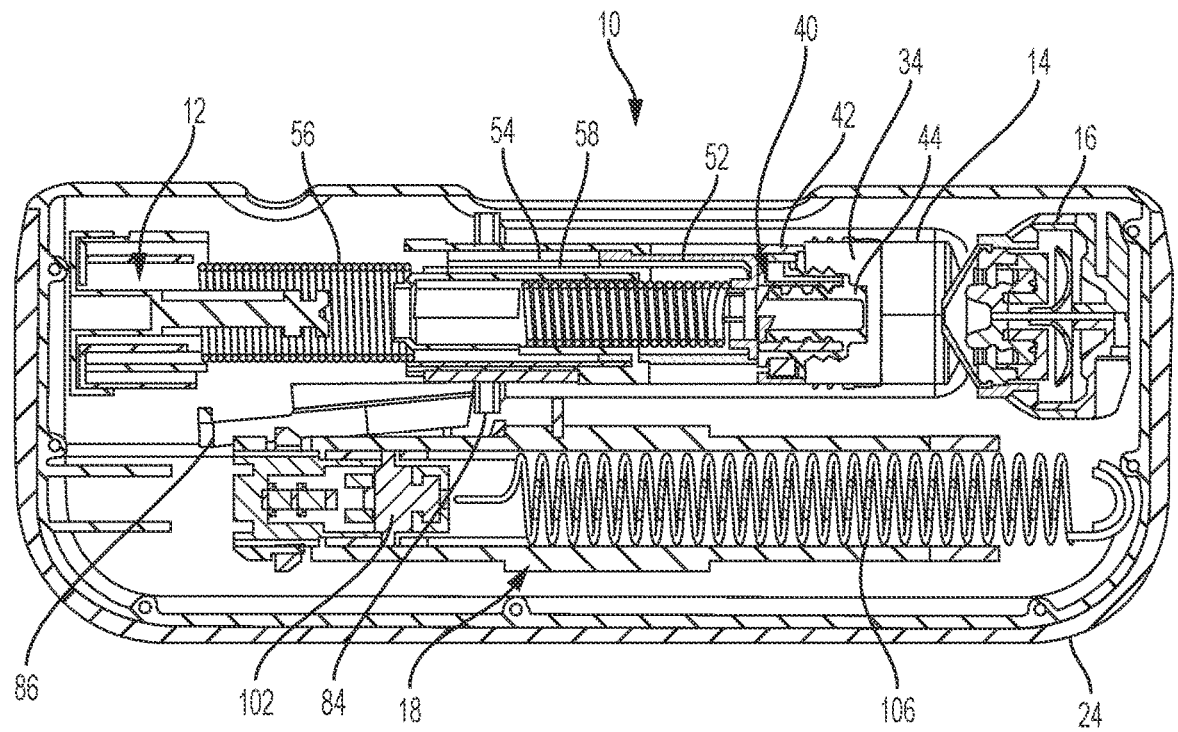
FIG. 11 is a top, cross-sectional view of the drug delivery system of FIG. 1 according to one aspect of the present invention, showing the drug delivery system in a use position.
Figure 12:
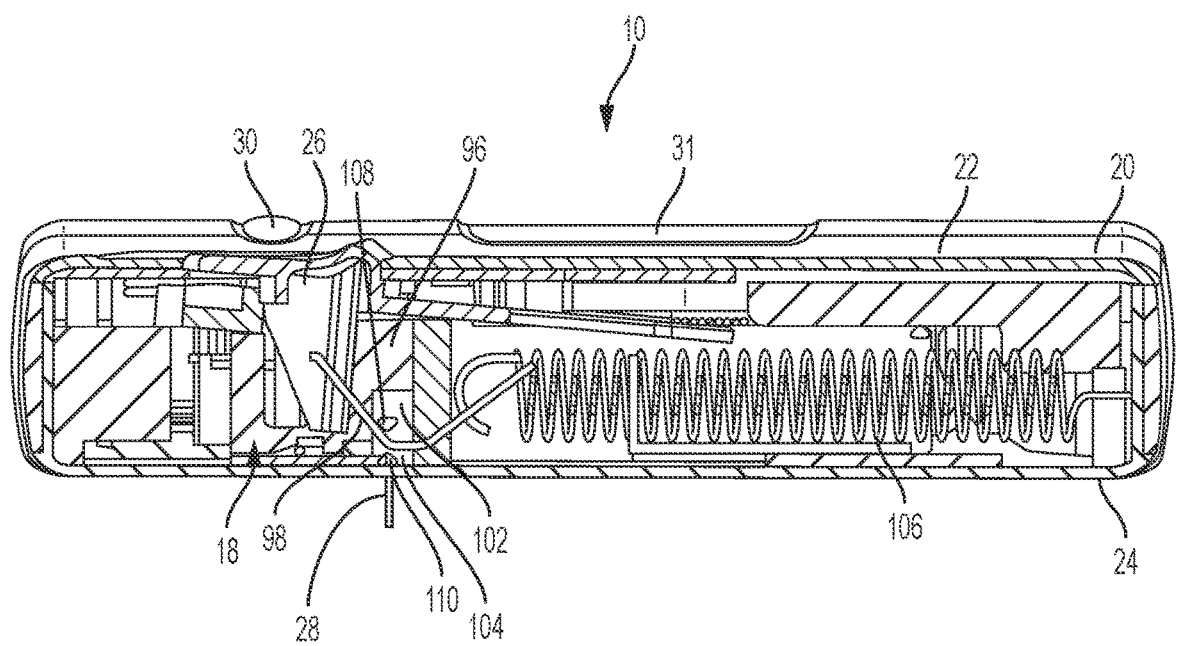
FIG. 12 is a front, cross-sectional view of the drug delivery system of FIG. 1 according to one aspect of the present invention, showing the drug delivery system in a use position.
Figure 13:
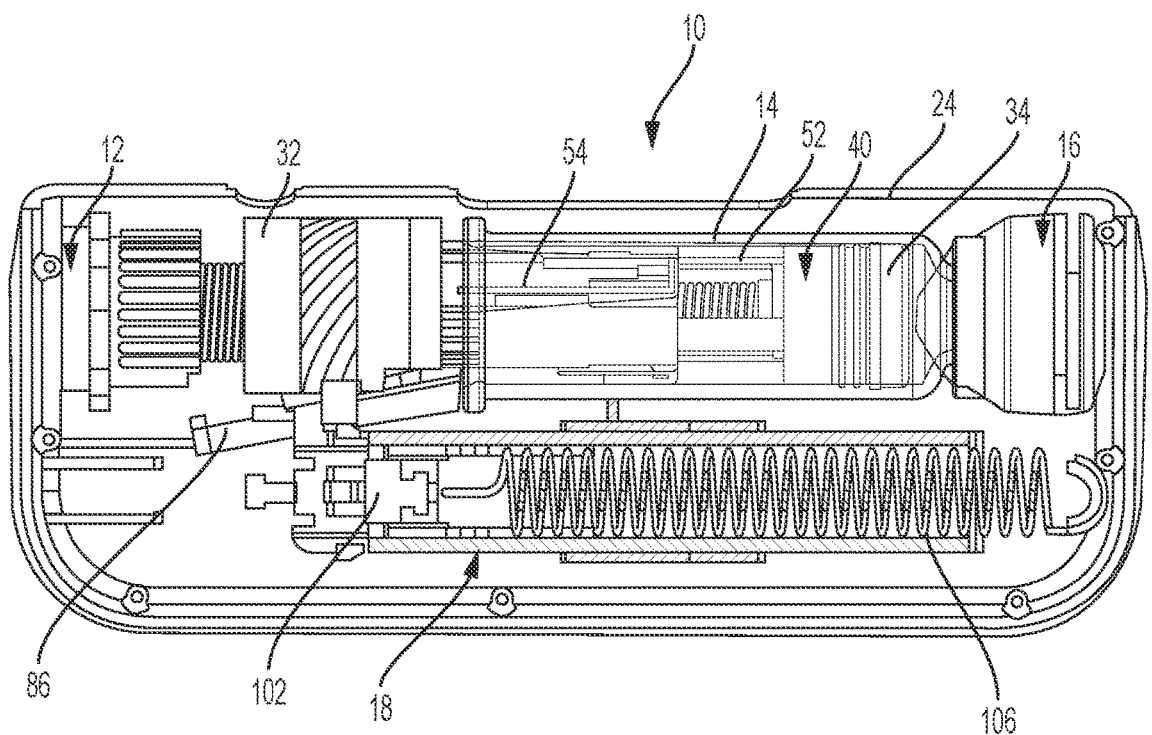
FIG. 13 is a top view of the drug delivery system of FIG. 1 according to one aspect of the present invention, showing a top portion of the housing removed and the drug delivery system in a post-use position.
Figure 14:
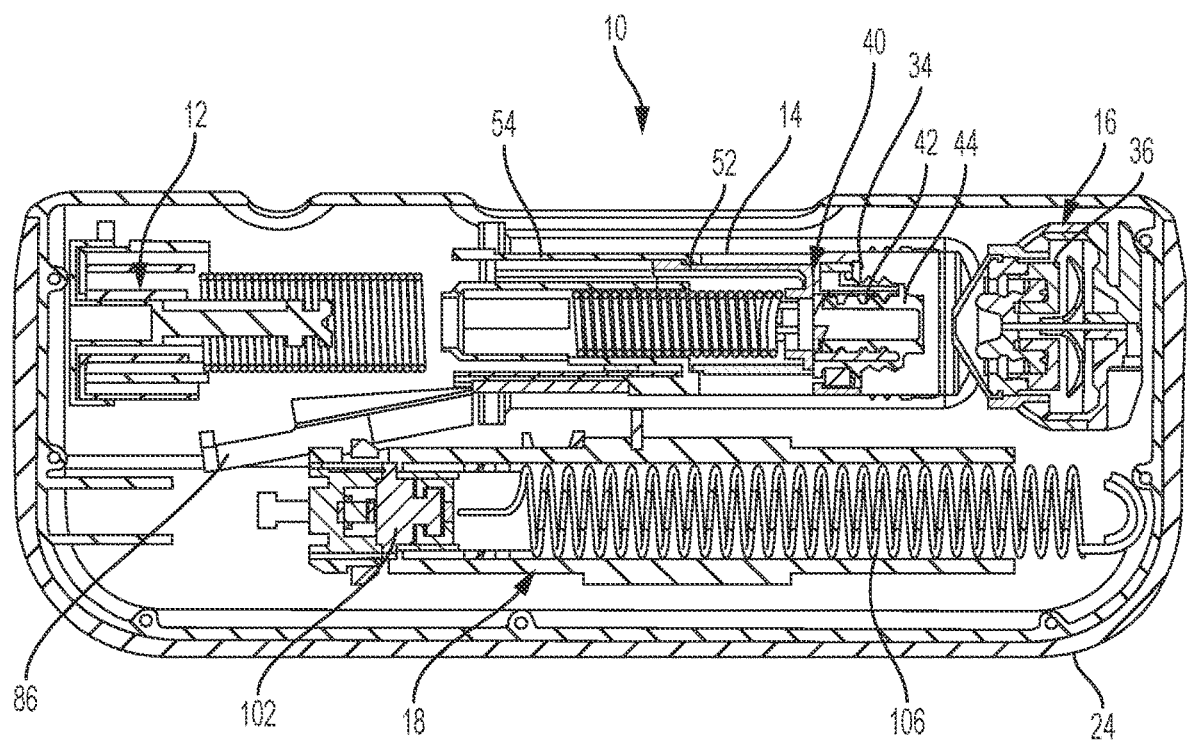
FIG. 14 is a top, cross-sectional view of the drug delivery system of FIG. 1 according to one aspect of the present invention, showing the drug delivery system in a post-use position.
Figure 15A:
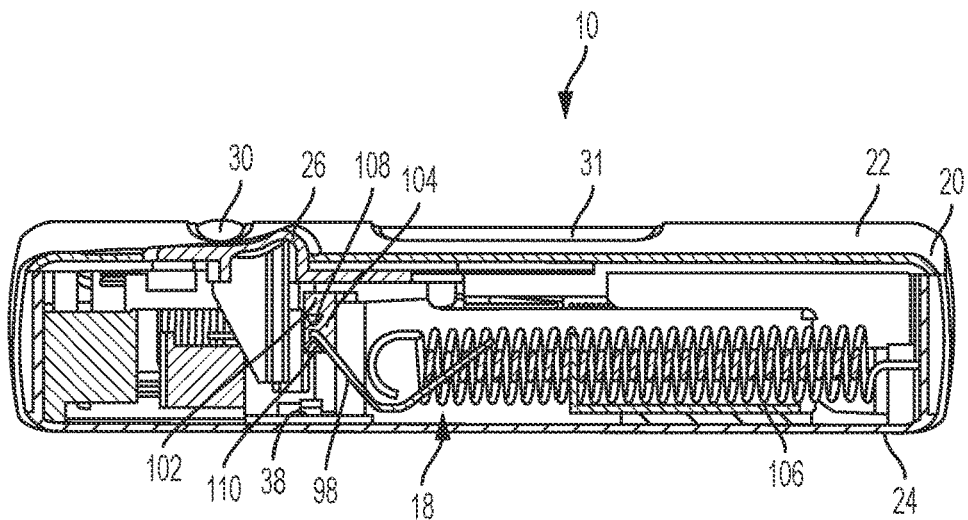
FIG. 15A is a front, cross-sectional view of the drug delivery system of FIG. 1 according to one aspect of the present invention, showing the drug delivery system in a post-use position.
Figure 15B:
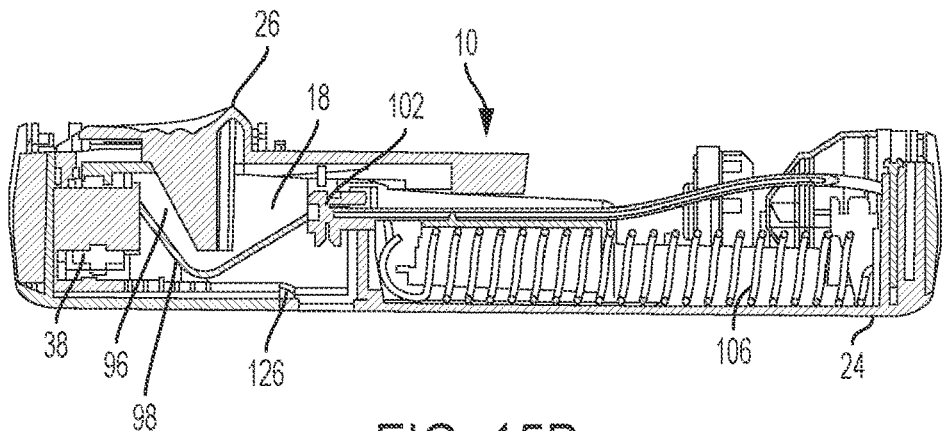
FIG. 15B is a front, cross-sectional view of the drug delivery system of FIG. 1 according to one aspect of the present invention, showing a pad with the drug delivery system in a pre-use position.
Figure 15C:
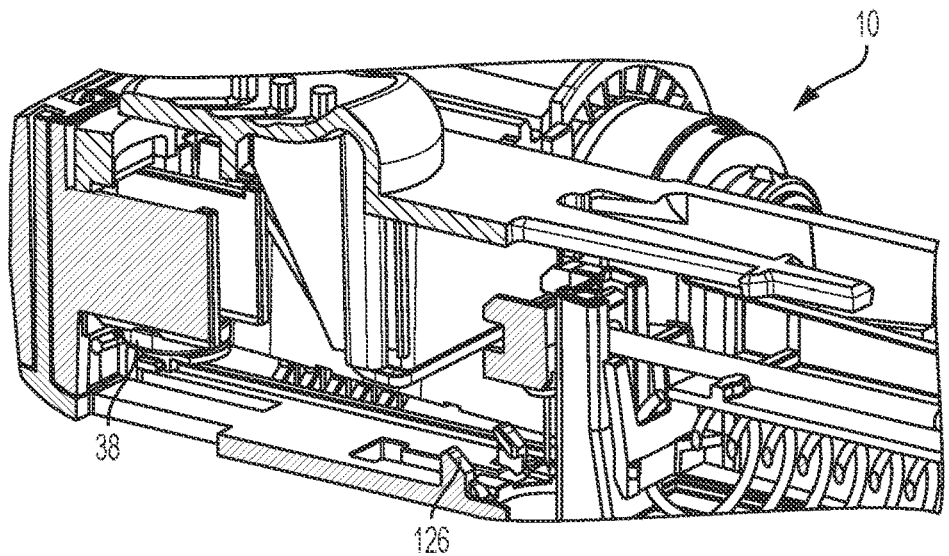
FIG. 15C is a perspective, cross-sectional view of the drug delivery system of FIG. 1 according to one aspect of the present invention, showing a pad with the drug delivery system in a pre-use position.
Figure 15D:
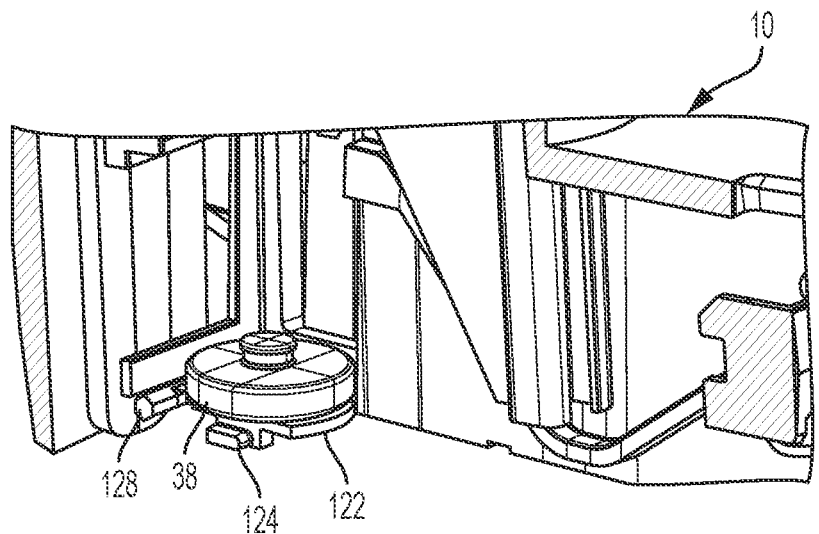
FIG. 15D is a perspective, cross-sectional view of the drug delivery system of FIG. 1 according to one aspect of the present invention, showing a pad with the delivery system in a pre-use position.
Figure 16:
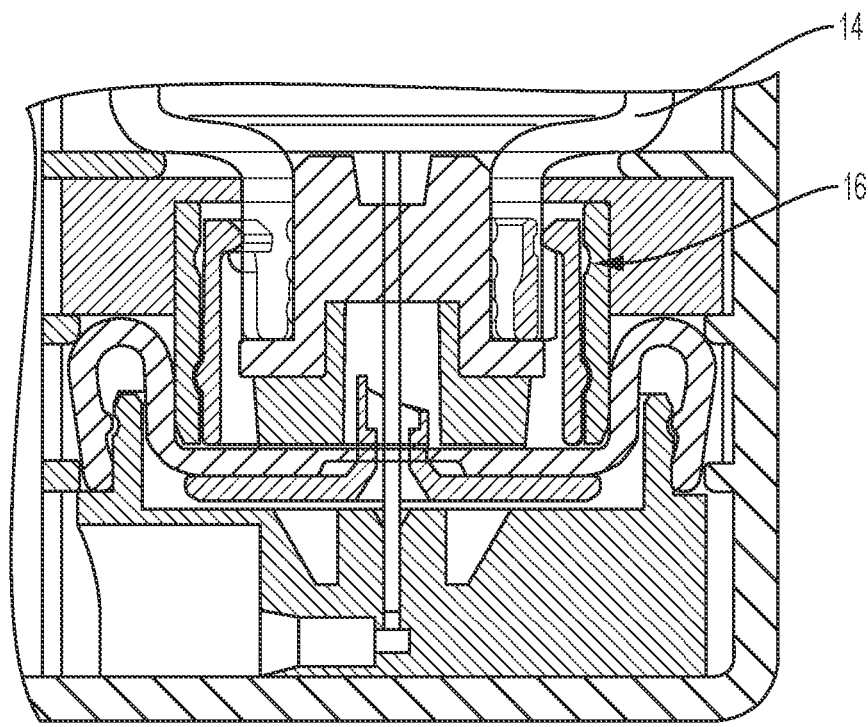
FIG. 16 is a partial cross-sectional view of the drug delivery system of FIG. 1 according to one aspect of the present invention, showing a valve assembly.

During the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15A, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Referring to FIGS. 15A-15D, the pad 38 is biased into the pad as the needle actuator body 96 moves from the use position to the post-use position. In particular, the pad 38 is received by a pad arm 122 having a cam surface 124 that cooperates with a cam track 126 on the bottom portion 24 of the housing 20. The pad arm 122 is connected to the needle actuator body 96 via a torsion bar 128. The cam surface 124 is configured to engage the cam track 126 to deflect the pad arm 122 downwards, thereby allowing the pad 38 to pass beneath the needle 28 before being biased upwards into the needle 28. The torsion bar 128 allows the pad arm 122 to twist about a pivot of the needle actuator body 96. The pad 38 may be press-fit into an opening of the pad arm 122, although other suitable arrangements for securing the pad 38 may be utilized.

With reference to FIGS. 1-18, the drive assembly 12 according to one aspect of the present invention is shown. As discussed above, the drive assembly 12 is configured to move the container 14 to pierce the closure 36 of the container 14 and also to move the stopper 34 within the container 14 to dispense fluid or medicament from the container 14. The drive assembly 12 is shown and described in further detail in the aforementioned U.S. Provisional Application No. 62/347,899 and is configured to engage and cooperate with a spacer assembly 40 received by the stopper 34 of the container. The spacer assembly 40 includes a spacer 42 and a spacer holder 44. The spacer holder 44 is received by the stopper 34 and the spacer 42 is received by the spacer holder 44. The spacer holder 44 includes a first threaded portion that engages a corresponding threaded portion of the stopper 34, although other suitable arrangements may be utilized. The spacer 42 also includes a threaded portion that engages a corresponding second threaded portion of the spacer holder 44 for securing the spacer 42 to the spacer holder 44, although other suitable arrangements may be utilized. The drive assembly 12 is configured to dispense a range of pre-determined fill volumes of the container 14 while maintaining the functional features of the system 10 described above, including, but not limited to, retraction of the needle 28 after the end of the dose and providing an indication of the status of the system 10 while also minimizing abrupt engagement of the stopper 34 by the drive assembly 12. The drive assembly 12 is configured to dispense a plurality of discrete fill volume ranges by utilizing a plurality of sizes of the spacers 42. In one aspect, twelve fill volume ranges and twelve spacer 42 sizes are provided. In one aspect, the length of the spacer 42 is changed to accommodate different fill volumes in the container 14. Alternatively, a single size spacer 42 may be utilized with a plurality of fill volumes in the container 14 accommodated by utilizing a plurality of shims that are received by the spacer 42.

With continuing reference to FIGS. 1-18, the drive assembly 12 includes a first plunger member 52, a second plunger member 54 received by the first plunger member 52 in a telescoping arrangement, a first biasing member 56, and a second biasing member 58. The first plunger member 52 is moveable from a pre-use position, to a use position, to a post-use position with the first plunger member 52 configured to engage the spacer assembly 40 and move the stopper 34 within the container 14 to dispense medicament from the container 14. The first plunger member 52 is configured to move axially. The second plunger member 54 and the first plunger member 52 form a telescoping arrangement with the second plunger 54 configured to move axially after the first plunger member 52 moves a predetermined axial distance. The movement of the first and second plunger members 52, 54 is provided by the first and second biasing members 56, 58, which are compression springs, although other suitable arrangements for the biasing members 56, 58 may be utilized.

The first biasing member 56 is received by the second plunger member 54 and is constrained between a plunger actuation member and an index member and a first spring seat of the second plunger member 54. The second biasing member 58 is positioned radially inward from the first biasing member 56 and received by the second plunger member 54. The second biasing member 58 is constrained between a second spring seat of the second plunger member 54 and the first plunger member 52. The second biasing member 58 is configured to bias the first plunger 52 member towards the container 14 from the pre-use position, to the use position, and to the post-use position. The first biasing member 56 is configured to bias the second plunger member 54 towards the container 14, which, in turn, biases the first plunger member 52 towards the container 14 from the pre-use position, to the use position, and to the post-use position. More specifically, the second biasing member 58 is configured to drive the first plunger member 52 against the spacer assembly 40 or stopper 34 to move the container 14 into engagement with the valve assembly 16, thereby piercing the closure 36 of the container 14 and placing the container 14 in fluid communication with the needle 28 via the tube 61, as shown in FIGS. 17 and 18. The first biasing member 56 is configured to move the stopper 34 within the container 14 to dispense the medicament within the container 14. The second biasing member 58 has a different spring constant than the first biasing member 56. In particular, the second biasing 58 member is stiffer than the first biasing member 56 to provide a high force for piercing the closure 36 of the container 14 while the first biasing member 56 provides a lower force for dispensing as appropriate for the viscosity of the fluid or medicament within the container 14.

Upon engagement of the actuator button 26 and release of the needle actuator assembly 18, which is discussed in more detail below, the needle actuator assembly 18 moves within the housing 20 from the pre-use position, to the use position, and to the post-use position. During the initial movement of the needle actuator assembly 18, a portion of the needle actuator assembly 18 engages a drive surface of a plunger actuation member to move the plunger actuation member 60 from the first rotational position to the second rotational position.

Referring to FIGS. 10-11, 13, and 17, the second plunger member 54 includes a plurality of coded projections 84 with a preselected one of the plurality of coded projections 84 configured to engage a restriction member of flipper member 86 of the system 10. As discussed in more detail below, the restriction member 86 cooperates with the needle actuation assembly 18 and restricts movement of the needle actuator assembly 18 from the use position to the post-use position until a predetermined end-of-dose position of the stopper 34 is reached. In one aspect, the restriction member 86 is configured to restrict axial movement of the needle actuation assembly 18 from the use position through engagement between the restriction member 86 and a portion of the needle actuation assembly 18. Such engagement between the restriction member 86 and the needle actuation assembly 18 is released by rotation of the restriction member 86 when the stopper 34 reaches the end-of-dose position. During the use position of the needle actuator assembly 18, the restriction member 86 is biased in a rotational direction with the rotation of the restriction member 86 being prevented through engagement between the restriction member 86 and one of the plurality of coded projections 84 of the second plunger member 54. The plurality of coded projections 84 may be axial ribs of varying length, although other suitable arrangements may be utilized. Each coded projection 84 defines a point at which the restriction member 86 is able to rotate, thereby releasing the needle actuator assembly 18. The smooth portion of the second plunger member 54 may also provide a further "code" for determining when the system 10 transitions to the end-of-dose position.

As discussed above, the indicator arrangement 32 moves with different portions of the indicator arrangement 32 visible through the indicator window 30 as the system 10 moves from the pre-use, use, and post-use or end-of-dose positions. More specifically, the indicator arrangement 32 engages a portion of the restriction member 86 and moves along with the restriction member 86 through the various stages of the system 10 to provide an indication to the user regarding the state of the system 10.

During assembly of the system 10, the dosage of the container 14 is matched with a specific spacer 42 having a set length and a corresponding one of the plurality of coded projections 84 is aligned with the restriction member 86. Accordingly, as discussed above, the container 14 may be provided with a plurality of dosage volumes with each volume corresponding to a specific spacer 42 and coded projection 84. Thus, even for different dosage volumes, the system 10 is configured to inject the needle 28 into the user to deliver a dose of medicament from the container 14, retract the needle 28 after the end of the dose, and provide an indication of the status of the system 10 while minimizing abrupt engagement of the stopper 34 by the drive assembly 12. In particular, the size of the stopper 34 may be selected to minimize the distance between the first plunger member 52 and the spacer assembly 40 and does not require the use of damping.

Referring again to FIGS. 1-18, the needle actuator assembly 18 according to one aspect of the present invention is shown. The needle actuator assembly 18 includes a needle actuator body 96 having guide surfaces 98, a needle shuttle 102 having cam surfaces 104, and the needle 28 received by the needle shuttle 102 and configured to be in fluid communication with the container 14 as discussed above. The needle actuator body 96 is generally rectangular with the guide surfaces 98 protruding radially inward. The needle shuttle 102 is received within the needle actuator body 96. As described above, the needle actuator body 96 is moveable within the housing 20 from a pre-use position (shown in FIGS. 4-6), an initial actuation position (FIGS. 7-9), a use position (FIGS. 10-12), and a post-use position (FIGS. 13-15A). The needle actuator body 96 is biased from the pre-use position to the post-use position via an extension spring 106, although other suitable biasing arrangements may be utilized. The needle actuator body 96 is released and free to move from the pre-use position to the use position upon engagement of the actuator button 26. The needle actuator body 96 moves from the use position to the post-use position after rotation of the restriction member 86.

With continued reference to FIGS. 1-18, the needle shuttle 102 is moveable along a vertical axis between a retracted position where the needle 28 is positioned within the housing 20 and an extended position where at least a portion of the needle 28 extends out of the housing 20. The needle shuttle 102 is configured to move between the retracted position and the extended position through engagement between the guide surfaces 98 of the needle actuator 96 and the cam surfaces 104 of the needle shuttle 102. The cam surfaces 104 are provided by first and second cam members 108, 110, with the first cam member 108 spaced from the second cam member 110. The housing 20 includes a guide post 112 having a recess configured to receive a T-shaped projection 114 on the needle shuttle 102, although other shapes and configurations may be utilized for the guide post 112 and T-shaped projection 114. The needle shuttle 102 moves along the guide post 112 between the retracted and extended positions. The guide post 112 is linear and extends about perpendicular from the housing 20, although other suitable arrangements may be utilized. The guide surfaces 98 of the needle actuator body 96 are non-linear and each include a first side and a second side positioned opposite from the first side.

As discussed below, the guide surfaces 98 of the needle actuator body 96 cooperate with the cam members 108, 110 of the needle shuttle 102 to move the needle shuttle 102 vertically between the retracted and extended positions as the needle actuator body 96 moves axially from the pre-use position to the post-use position. The needle shuttle 102 also includes a shuttle biasing member (not shown) configured to engage the housing 20 or the actuator button 26. In particular, the shuttle biasing member engages the housing 20 or actuator button 26 and provides a biasing force when the needle actuator body 96 is transitioning from the use position to the post-use position. When the needle actuator body 96 is fully transitioned to the post-use position, the cam members 108, 110 of the needle shuttle 102 are disengaged from the guide surfaces 98 of the needle actuator body 96 and the shuttle biasing member biases the needle shuttle 102 downward such that the needle 28 engages the pad 38, as discussed above. As discussed above in connection with FIGS. 1-18, however, the pad 38 may also be biased into the needle 28 rather than biasing the needle shuttle 102 downwards via the shuttle biasing member 120. The needle actuator body 96 may interact with the actuator button 26 to prevent the actuator button 26 from popping back up until the post-use position is reached, which is discussed below in more detail.

Referring to FIGS. 3-15D, in a pre-use position (FIGS. 5-6), the needle shuttle 102 is in the retracted position with the cam members 108, 110 spaced from the guide surface 98 of the needle actuator body 96. As the needle actuator body 96 moves to the use position (FIGS. 10-12), the second cam member 110 of the needle shuttle 102 engages the guide surfaces 98 to move the needle shuttle 102 from the retracted position to the extended position. During the transition from the use position to the post-use position of the needle actuator body 96 (FIGS. 13-15A), the first cam member 108 of the needle shuttle 102 continues to engage the guide surfaces 98 to move the needle shuttle 102 from the extended position to the retracted position. After the needle actuator body 96 is fully transitioned to the post-use position, the shuttle biasing member biases the needle shuttle 102 downward as the cam members 108, 110 disengage from the guide surfaces 98 of the needle actuator body 96 with the needle 28 engaging the pad 38.

Figure 19A:
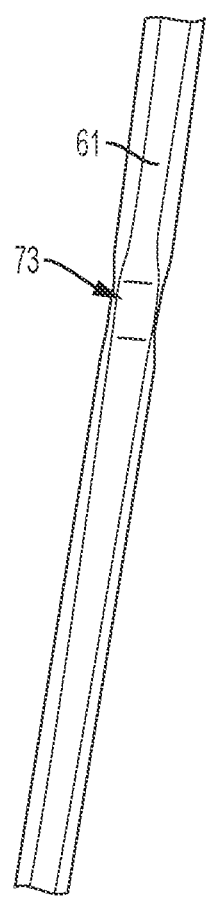
FIG. 19A is a perspective view of the end-of-dose detection member of FIG. 17 in an uninflated condition according to one aspect of the present invention.
Figure 19B:
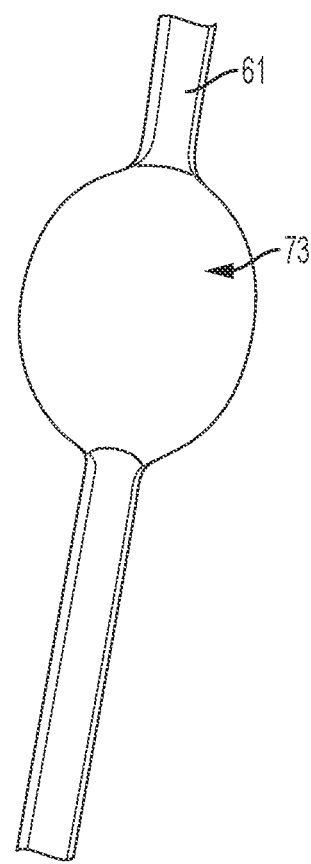
FIG. 19B is a perspective view of the end-of-dose detection member of FIG. 17 in an inflated condition according to one aspect of the present invention.

Reference is now made to FIGS. 17-18 and 19A-19B, which show the end-of-dose detection arrangement, generally indicated as 71. The end-of-dose arrangement functions as an inline pressure sensor for preventing movement of the needle actuator during delivery of the fluid and for controlling the withdrawal of the needle 28 from the patient at the end of the medicament dose. The end-of-does detection arrangement 71 includes an expandable portion or balloon 73 in the tube 61 that is in fluid communication with the container 14 and the needle 28. The expandable portion 73 is configured to expand upon actuation of the drive assembly 12 during delivery of the medicament to prevent movement of the needle actuator assembly 18 and withdrawal of the needle 28. The expandable portion 73 is also configured to deflate or to be in a non-expanded state at the end of the dose of medicament due to a drop in pressure from the medicament due to lack of medicament within the container 14. When the expandable portion is in the non-expanded state, as shown in FIG. 19A, the needle actuator assembly 18 is permitted to move to the post-use position, thus, retracting the needle 28 from the patient. One example of the tube 61 including the expandable portion 73 can be a SmartForm™ balloon tube available from Creganna Tactx Medical, however, it can be appreciated that other balloon tubing can be utilized in the invention. It can also be appreciated that the end-of-dose detection arrangement 71 can be used with either a drug delivery device or an injector.

With continued reference to FIGS. 17-18, according to one embodiment, a portion of the tube 61 rides in a slot 75 on a top portion 77 of the needle actuator assembly 18. When the device 10 is activated, the needle actuator assembly 18 is stopped by a restriction member or flipper 86 riding on the stopper or plunger member 34 as the needle 28 is inserted into the patient. Pressure in the fluid path increases and the expandable portion 73 expands or inflates. Motion of the stopper or plunger member 34 releases the restriction member or flipper 86 allowing the needle actuator assembly 18 to be retained by the expandable portion 73 while the needle remains in the patient. As the pressure in the fluid path or tube 61 decreases at the end of the dose, the expandable portion 73 deflates and permits the needle actuator assembly 18 to retract the needle 28 from the patient.

The use of the end-of-dose arrangement 71 of the present invention allows the stopper or plunger member 34 to bottom out within the container 14 and to still automatically withdraw the needle 28 from the patient after the end of the dose.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery system for injecting a medicament, the system comprising:

a container configured to deliver a medicament;

a drive assembly which, upon actuation, is configured to expel the medicament from the container;

a needle for injecting the medicament to a patient;

a needle actuator assembly comprising a movable portion biased by a biasing member and configured to move the needle between a pre-use position, a use position for delivery of the medicament to the patient, and a post-use position after delivery of the medicament is completed; and a tube in fluid communication with the container and the needle, the tube comprising an expandable portion having a radially expanded state and a non-expanded state, wherein the expandable portion is configured to be in the radially expanded state upon actuation of the drive assembly and a non-expanded state when the needle is in the post-use position;

wherein the expandable portion comprises a balloon in the tube that inflates into the radially expanded state upon actuation of the drive assembly.

2. The system of claim 1, wherein the expandable portion of the tube is in the non-expanded state when the needle is in the pre-use position.

3. The system of claim 1, wherein the movable portion of the needle actuator assembly engages the expandable portion of the tube when the expandable portion of the tube is in the expanded state.

4. The system of claim 3, wherein engagement between the needle actuator assembly and the tube is released when the tube is in the non-expanded state, permitting the needle actuator assembly to move and retract the needle.

5. The system of claim 1, wherein the expandable portion of the tube is configured to be placed in the expanded state by a pressure within the container caused by actuation of the drive assembly.

6. The system of claim 5, wherein the expandable portion of the tube is configured to change from the expanded state to the non-expanded state when the pressure within the container caused by the actuation of the drive assembly is reduced due to a lack of medicament within the container.

7. The system of claim 1, further comprising a housing enclosing at least a portion of the container, the drive assembly, the needle, the needle actuator assembly, and the tube.

8. The system of claim 7, wherein at least a portion of the needle is extended from the housing in the use position.

9. The system of claim 1, wherein the tube is associated with the needle actuator assembly.

10. The system of claim 9, including a slot in the needle actuator configured for receiving a portion of the tube.

11. The system of claim 1, wherein the expandable portion of the tube comprises a balloon.

12. A drug delivery system for injecting a medicament, the system comprising:

a container configured to deliver a medicament;

a drive assembly which, upon actuation, is configured to expel the medicament from the container;

a needle for injecting the medicament to a patient;

a needle actuator assembly comprising a movable portion biased by a biasing member and configured to move the needle between a pre-use position, a use position for delivery of the medicament to the patient, and a post-use position after delivery of the medicament is completed;

a tube connecting the container to the needle; and an end-of-dose detection assembly which prevents movement of the needle actuator during delivery of the medicament, wherein the end-of-dose detection assembly comprises a balloon disposed in the tube that inflates into a radially expanded state upon actuation of the drive assembly and during delivery of the medicament and that deflates at the end of dose to allow movement of the needle.

13. The drug delivery system of claim 12, wherein the balloon deflates due to a drop in pressure in a fluid path defined between the container and the needle.

14. The drug delivery system of claim 12, wherein the balloon expands radially during delivery of the medicament.

15. The drug delivery system of claim 12, wherein the end-of-dose detection assembly is configured to permit the needle actuator assembly to move to the post-use position when the balloon is in a non-expanded state.

16. The drug delivery system of claim 12, wherein the end-of-dose detection assembly is configured to retain the needle assembly when the balloon is in an expanded state.

17. The drug delivery system of claim 12, further comprising:

a stopper configured to move with the container to expel the medicament from the container; and a restriction member configured to restrict movement of the needle actuator assembly from the use position to the post-use position until a predetermined end-of-dose position of the stopper is reached, wherein motion of the stopper releases the restriction member, such that the end-of-dose detection assembly retains the needle actuator assembly in the use position.

* * * * *

UNITED STATES PATENT AND TRADEMARK OFFICE
CERTIFICATE OF CORRECTION

PATENT NO. : 12,343,513 B2  
APPLICATION NO. : 17/850428  
DATED : July 1, 2025  
INVENTOR(S) : David E. Booth et al.

Page 1 of 1

It is certified that error appears in the above-identified patent and that said Letters Patent is hereby corrected as shown below:

On the Title Page

Column 2, item (57), Abstract, Line 9, delete "positon" and insert -- position --

Column 2, item (57), Abstract, Line 17, delete "positon." and insert -- position. --

In the Claims

Column 11, Line 49, Claim 10, after "actuator" insert -- assembly --

Signed and Sealed this  
Nineteenth Day of August, 2025

Coke Morgan Stewart  
*Acting Director of the United States Patent and Trademark Office*